US007008961B1

(12) United States Patent
Arcadi

(10) Patent No.: US 7,008,961 B1
(45) Date of Patent: Mar. 7, 2006

(54) COMPOSITION AND METHOD FOR TREATING CARCINOMA

(75) Inventor: John A. Arcadi, deceased, late of Whittier, CA (US); by Doris M. Arcadi, legal representative, Whittier, CA (US)

(73) Assignee: Huntington Medical Research Institutes, Pasadena, CA (US)

( * ) Notice: Subject to any disclaimer, the term of this patent is extended or adjusted under 35 U.S.C. 154(b) by 0 days.

(21) Appl. No.: 09/383,114

(22) Filed: Aug. 25, 1999

Related U.S. Application Data

(63) Continuation-in-part of application No. 08/816,411, filed on Mar. 13, 1997, now abandoned, which is a continuation of application No. 08/516,004, filed on Aug. 16, 1995, now abandoned.

(51) Int. Cl.
 *A61K 33/35* (2006.01)
(52) U.S. Cl. ..................................................... 514/454
(58) Field of Classification Search ................. 514/454
 See application file for complete search history.

(56) References Cited

U.S. PATENT DOCUMENTS

| 5,189,029 | A |   | 2/1993  | Boyer et al. ................... 514/64  |
| 5,260,327 | A |   | 11/1993 | Kim et al. .................... 514/405 |
| 5,360,803 | A |   | 11/1994 | Shishido et al. ........... 514/224.2 |
| 5,880,141 | A | * | 3/1999  | Tang et al. ................... 514/339 |

OTHER PUBLICATIONS

Arcadi, J. Surgical Oncology, 44:103-108, 1990.*
Arcadi, Urology, 28(6), 501-503, Dec. 1986.*
Bernal et al., Science (1983), 222(4620), 160-72 Abstract Only.*
EMBASE AN 04120900, Montaguti et al, Arzneimittle-Forschung/Drug Research, 1994, 44/4 566-570, abstract.*
EMBASE 94148842, Gupta et al, PDA J. Pharmac. Sci. Tech, 1994 48/2 86-91, abstract.*
MEDLINE AN 93172422, Kaplan et al, J. Urology, Mar. 1993 149(3) 519-22, abstract.*
Stone et al., "Isolation of a Human Prostate Carcinoma Cell Line (DU 145)", *Int. J. Cancer*, vol. 21, No. 3, Mar. 15, 1978, pp. 274-281.
Kaighn, et al., "Establishment and Characterization of a Human Prostatic Carcinoma Cell Line (PC-3)", *Investigative Urology*, vol. 17, No. 1, Jul., 1979, pp. 16-23.
Johnson et al., "Localization of Mitochondria in Living Cells with Rhodamine 123", *Cell Biology, Proc. Natl. Acad. Sci. USA*, Feb. 1980, pp. 990-994.
Peehl et al., "Clonal Growth of Human Keratinocytes with Small Amounts of Dialyzed Serum", In Vitro, vol. 16, No. 6, Jun. 1980, pp. 526-540.

Lampidis et al., "Selective Toxicity of Rhodamine 123 in Carcinoma Cells In Vitro", *Cancer Research*, vol. 43, Feb. 1983, pp. 716-720.
Bernal et al., "Rhodamine-123 Selectively Reduces Clonal Growth of Carcinoma Cells in Vitro", *Science*, vol. 218, Dec. 10, 1982, pp. 1117-1119.
Horoszewicz et al., "LNCaP Model of Human Prostatic Carcinoma", *Cancer Research*, vol. 43, Apr. 1983, pp. 1809-1818.
Bernal et al., "Anticarcinoma Activity in vivo of Rhodamine 123, a Mitochrondrial-Specific Dye", *Science*, vol. 222, Oct. 14, 1983, pp. 169-172.
Lampidis et al., "Selective Killing of Carcinoma Cells <<in vitro>> by Lipophilic-Cationic Compounds: a Cellular Basis", Biomed. Pharmacother., vol. 39, 1985, pp. 220-226.
Pollard et al., "Autochthonous Prostate Adenocarcinomas in Lobuund-Wistar Rats: A Model System", *The Prostate*, vol. 11, No. 3, 1987, pp. 219-227.
Alley et al., "Feasibility of Drug Screening with Panels of Human Tumor Cell Lines Using a Microculture Tetrazolium Assay", *Cancer Research*, vol. 48, Feb. 1, 1988, pp. 589-601.
Herr et al., "Anticarcinoma Activity of Rhodamine 123 Against a Murine Renal Adenocarcinoma", *Cancer Research*, vol. 48, Apr. 15, 1988, pp. 2061-2063.
Goffney et al., "In Vitro and in Vivo Cytotoxicity of Rhodamine 123 Combined with Hyperthermia", *Cancer Research*, vol. 50, Feb. 1, 1990, pp. 459-463.
Stamey et al., "Adenocarcinoma of the Prostate", *Campbell's Urology*, Sixth Edition, Philadelphia, W.B. Saunders Co., 1992, pp. 1159-1221.
Sun et al., "AA1, a Newly Synthesized Monovalent Lipophilic Cation, Espresses Potent in Vivio Antitumor Activity", *Cancer Research*, vol. 54, Mar. 15, 1994, pp. 1465-1471.
Ara, et al., "cis-Diamminedichloroplatinum(II) Resistant Human Tumor Cell Lines are Collaterally Sensitive to $PtCl_4(Rh-123)_2$: Evidence for Mitochondrial Involvement", *Cancer Research*, vol. 54, Mar. 15, 1994, pp. 1497-1502.
Taplin et al., "Mutation of the Androgen-Receptor Gene in Metastatic Androgen-Independent Prostate Cancer", *The New England Jour. of Medicine*, vol. 332, No. 21, May 25, 1995, pp. 1393-1398.

(Continued)

*Primary Examiner*—Rebecca Cook
(74) *Attorney, Agent, or Firm*—Christie, Parker & Hale, LLP

(57) ABSTRACT

Carcinoma is treated in a patient by administration of Rhodamine-123 (Rh-123) orally or by intravenous injection of a treatment solution of Rh-123, ethyl alcohol, dextrose, and water in an amount sufficient to effect in vivo destruction of cancer cells. The treatment solution is made by mixing a stock solution of Rh-123 in a solution of 95% ethyl alcohol and 5% water (by volume) with a solution of 5% (by weight) dextrose in water. For prostate cancer, treatment is controlled by measuring the level of prostate specific antigen (PSA), or prostate specific acid phosphatase in the blood of the patient.

30 Claims, 9 Drawing Sheets

OTHER PUBLICATIONS

"Set 23: Potential-Sensitive Probes", excerpt from Molecular Probes, Inc. literature (undated).

Fierz-David et al., Information About Mono-Äthyl-O-Toluidins and Some Rhodamines Obtainable Therefrom, *Helv, Chem., Heta*, 1934, pp. 1452-1459, with English translation.

Weiss et al., *Kodak Laboratory Chems. Bulletin*, vol. 55, No. 2, 1984.

Banes et al., "High-Performance Liquid Chromatographic Quantitation of Rhodamines 123 and 110 From Tissues and Cultured Cells", *J. of Chromatrography*, 356, 1986, pp. 301-309.

Arcadi, "Rhodamine-123 as Effective Agent in Rat Prostate Tumor R3327-H", *Urology*, vol. XXVII, No. 6, Dec. 1986.

Castro et al., "Rhodamine-123 as a New Laser Dye: In Vivo Study of Dye Effects on Murine Metabolism, Histology and Ultrastructure", *Laryngoscope 99*, Oct. 1989, pp. 1057-1062.

Arcadi, "Use of Rhodamine 123 in the Treatment of the Pollard III Rat Prostate Adenocarcinoma", *J. of Surg. Oncology*, 1990, pp. 103-108.

Castro et al., "Photodynamic Therapy Using Rhodamine-123 as a New Laser Dye: Biodistribution, Metabolism and Histology in New Zealand Rabbits", *Laryngoscope 101*, Feb. 1991, pp. 158-164.

Arcadi et al., "Studies of Rhodamine-123: Effect on Rat Prostate Cancer and Human Prostate Cancer Cells in Vitro", *J. of Surg. Oncology*, 1995, pp. 86-93.

Wong et al., "Removal of Carcinoma Cells from Contaminated Bone Marrow Using the Lipophilic Cation Rhodamine 123", *Clinical Cancer Research*, vol. 1, Jun. 1995, pp. 621-630.

* cited by examiner

COMPOSITION AND METHOD FOR TREATING CARCINOMA

CROSS-REFERENCE TO RELATED APPLICATION(S)

This is a continuation-in-part of application Ser. No. 08/816,411, filed March 13, 1997, abandoned which is a continuation of application Ser. No. 08/516,004, filed Aug. 16, 1995 abandoned.

This invention relates to compositions and methods for treating carcinoma, i.e., a malignant tumor of epithelial origin, with Rhodamine-123 (methyl o-(6-amino-3-imino-3H-xanthen-9-yl) benzoate monohydrochloride).

BACKGROUND OF THE INVENTION

Metastatic hormone refractory prostate cancer, one of many carcinomas, such as cancer of the breast, liver, pancreas, bladder, lung, skin, colon, and the like, responds poorly to chemotherapy because of its slow rate of replication. It accounts for about 40,000 deaths annually. There has been no satisfactory treatment for metastatic, hormone refractory prostate cancer. Patients with the disease die with diffuse pain, obstructive renal failure, and bone marrow failure due to replacement by the tumor. Treatment of carcinoma needs an agent which is effective independently of the rate of cell division or the ability to interfere with DNA or RNA metabolism.

Rhodamine-123 (Rh-123) is such an agent. It preferentially localizes in the mitochondria of malignant living cells because of a difference in the plasma membrane potential of normal and malignant cells, together with the positive charge on this lipophilic molecule. Therefore, Rh-123 is selectively toxic for carcinoma cells. In 1986, I reported the effect of a saline suspension of Rh-123 on the transplantable rat prostate tumor R3327-H (Dunning). The Rh-123 solution was administered subcutaneously every other day at a dosage of 15 mg/kg body weight. There was significant destructive alteration of the acinar cells with disruption of the cells from the basement membrane, destruction of the cytoplasm, as well as vacuolization and change in fibroblast shape and density.

In 1990, I reported the highly malignant, androgen-independent transplantable tumor designated P-A III to be highly sensitive to Rh-123 dissolved in DMSO. The Rh-123 treatment of the tumor resulted in significant destruction of tumor cells, with no toxicity noted in normal cells. Injection of tumor remnants into untreated susceptible Lobund-Wistar (L-W) rats produced no tumor growth.

In terms of a process, my invention provides a method for treating a patient with carcinoma by administration of Rhodamine-123 (Rh-123) in an amount sufficient to effect in vivo destruction of the cancer cells. Preferably, the Rh-123 is administered intravenously in a solution of ethyl alcohol and water. Preferably, the solution includes dextrose, and each dose of Rh-123 is administered to the patient by infusion with between about 10 and about 250 ml of the Rh-123 solution over a period between about 15 minutes and about 4 hours. The concentration of Rh-123 in the infused solution can be any convenient amount, but normally is between about 1 and about 20 mg/ml.

In another embodiment, the Rh-123 is administered orally either as a liquid, or as a pill, such as a tablet or capsule. Preferably, the pill releases the Rh-123 over an extended period of time, say, 2 to 24 hours, to avoid toxicity.

Preferably, the patient is treated with intermittent doses of Rh-123, which are generally increased from about 0.5 mg of Rh-123 per kg of patient weight up to about 30 mg per kg of patient weight, or until toxicity is observed, whichever comes first. In the case of prostate cancer, the treatment is continued until the level of prostate specific antigen (PSA) or prostate specific acid phosphatase in the patient's blood decreases significantly from the level prevailing in the patient just prior to treatment in accordance with this invention.

The Federal Food and Drug Administration (FDA) prefers that the administration of therapeutic agents be reported on the base of the surface area of the patient, which is calculated in accordance with the weight and height of the patient. For a typical prostate cancer patient, 1 kg of patient weight is equivalent to about 0.025 $m^2$ of surface area.

In terms of composition of matter, the invention provides a solution for treating a patient with carcinoma. The solution comprises ethyl alcohol and Rh-123 dissolved in water. Preferably, the solution also includes about 5% by weight of a sugar, such as dextrose or glucose, susceptible to metabolic assimilation.

The invention also provides a stock solution for preparing an administration solution used in treating carcinoma. The stock solution comprises Rh-123 dissolved in ethyl alcohol (preferably 95% ethyl alcohol and 5% water). The concentration of the Rh-123 in the stock solution is between about 5 and about 25 mg per ml.

These and other aspects of the invention will be more fully understood from the following description and the accompanying drawings.

DESCRIPTION OF THE PREFERRED EMBODIMENTS

The following describes my studies of:
1) the toxicity of DMSO, alcohol-glucose, and Rh-123 in mice;
2) the effect of Rh-123 on the autochthonous rat prostate adenocarcinoma produced in L-W rats by the injection of N-methyl-N-nitrosourea (MNU) and testosterone propionate (TP); and
3) the effect of Rh-123 on various human prostate cancer cell lines.

These studies include the effect of Rh-123 on clonogenicity (plating efficiency), Rh-123 uptake and retention, and Rh-123-induced cytotoxicity. The studies were done with Rh-123, laser grade, $C_{21}H_{17}ClN_2O_3$ with a molecular weight of 380.83 purchased from the Eastman Kodak Company (Rochester, N.Y.). Rh-123 has the following structure:

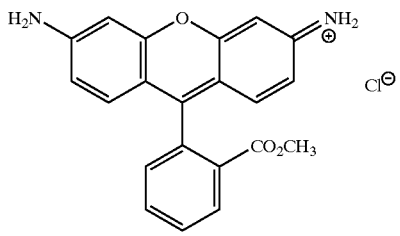

Toxicity Studies on Mice

The toxicity of two solvents for Rh-123, DMSO and alcohol-glucose, was studied in 60-day-old Swiss Webster mice (Simonsen Laboratories, Inc., Gilroy, Calif.). For each solvent there were five groups of five mice each, with the Rh-123 dose per group being 0, 2.0, 7.5, 15, and 20 mg/kg of body weight. A sixth group of five mice were not given any solvent or Rh-123. The solvents, with and without Rh-123, were administered at a concentration of 50% by volume DMSO in distilled water, and 5% alcohol by volume in a 5% by weight solution of glucose in distilled water. The glucose can be replaced by dextrose, fructose, or any suitable sugar susceptible to metabolic assimilation. The concentration of Rh-123 was 5 mg/ml. Appropriate controls were utilized. The mice were injected subcutaneously every other day for 2 weeks.

Three of five mice died at a dose of 20 mg/kg Rh-123 in DMSO; one of five mice died at 15 mg/kg Rh-123 in DMSO. Two of five mice died that received only 50% DMSO. Using the alcohol-glucose solution as a diluent, the mice tolerated a dose of 20 mg/kg of Rh-123 given every other day for a period of 2 weeks with no mortality.

Rat Prostate Adenocarcinoma

To determine the effectiveness of Rh-123 on induced autochthonous rat prostate adenocarcinoma developed within the prostate gland and seminal vesicles of L-W rats, thirteen L-W rats were inoculated intravenously with acidified MNU (30 mg/kg of body weight (BW)). Following the single inoculation of MNU, the rats were each implanted subcutaneously with 50 mg TP sealed in a silastic tube. Three implants of TP were administered, each at intervals of 2 months. After a latent period of 4–6 months, small palpable tumors were detected in the abdomen. The rats were then administered Rh-123 (15 mg/kg BW) subcutaneously every other day for six doses. The Rh-123 was dissolved in a 5% (by volume) ethanol-5% (by weight) glucose solution in sterile water at a concentration of 5 mg/ml. The rats were sacrificed 1 week after the last dose of Rh-123 and their tissues were fixed in 10% formalin.

Figure 1A:
FIG. 1a is a microscopic photograph showing untreated autochthonous rat prostate complex adenocarcinoma (ARPCA)
Figure 1B:
FIG. 1b is a microscopic photograph of ARPCA treated with Rh-123 at the rate of 15 mg/kg body weight every other day for six doses.
Figure 1C:
FIG. 1c is a microscopic photograph of ARPCA treated as the material shown in FIG. 1b.
Figure 1D:
FIG. 1d is a microscopic photograph of ARPCA treated as in FIG. 1b.

No gross changes were noted in the tumor mass of the prostate complex. Microscopic examination of the treated rats' prostate complexes revealed tumor tissue with marked cellular and acinar destruction, pyknosis, cytoplasmic smearing, and intraepithelial cyst formation. The effect of the treatment is shown by FIGS. 1a–1d. FIG. 1a shows an untreated autochthonous rat prostate complex adenocarcinoma (ARPCA). Note the irregular nuclei with prominent nucleoli. Cytoplasm is plentiful and well defined. FIG. 1b shows the effect of ARPCA treated with Rh-123 (15 mg/kgbw) every other day for six doses. The cytoplasm is greatly decreased in volume, and the nuclei are smaller and less distinct. Cyst formation is shown in both acini (arrows). FIG. 1c shows ARPCA treated as just described for FIG. 1b. Large cyst of cytoplasm between two nuclei is shown. FIG. 1d shows ARPCA treated as described as for FIG. 1b. Note the smudging and loss staining of cytoplasm. Nuclear detail is also lost. Hemotoxylin- and eosin-stained sections are present. The original magnification for the photographs shown in FIGS. 1a–1d is 400×. The tumor mass did not decrease in size presumably because of the accumulated debris of dead and dying cells. Normal surrounding tissue showed no change. Thus, Rh-123 was found to be a potent antitumor drug without causing adverse effects on normal tissue.

Studies of Human Prostate Cancer Cells In Vitro

Assays of Rh-123 toxicity were done with three human prostate cancer cell lines, PC-3 (Kaighn M E, Narayan K S, Ohnuki Y, et al.: Establishment and characterization of a human prostatic carcinoma cell line, *Invest Urol* 17:16–23, 1979), DU-145 (Stone K R, Mickey D, Wunderli H, et al.: Isolation of a human prostatic carcinoma cell line (DU145), *Int J Cancer* 21:274–281, 1978), and LNCaP (Horoszewitz J, Leong S, Kawinski E, et al.: LNCaP model of human prostatic carcinoma, *Cancer Res* 43:1809–1818, 1983), and a non-tumorigenic diploid prostate fibroblast cell strain (NPF-209) derived in our laboratories from a normal adult prostate. The NPF cells were used as controls, i.e., for comparison. The cells were maintained in disposable plastic culture vessels in a 1:1 mix of Dulbecco's modified Eagle's medium and Ham's F12 (DMEM/F12, from Sigma Chemical Co, St. Louis, Mo.) supplemented with 10% fetal bovine serum (FBS, from HyClone Labs, Inc., Logan, Utah). 3-[4, 5-Dimethylthiazol-2-yl]-2,5-diphenyltetrazolium bromide (MTT), DMSO, and other chemicals were also obtained from Sigma.

Rh-123 was dissolved in high purity water (Milli Q, Millipore Corp., Bedford, Mass.) at 2 mg/ml and sterilized by 0.2 μm filtration before use to provide a standard solution for cell cultures. Two different in vitro assays were used to assess cell viability following Rh-123 treatment, namely, i) colony formation by a clonal assay procedure (Peehl D M, Ham R G: Clonal growth of human keratinocytes with small amounts of dialyzed serum, *In Vitro* 16:526–538, 1980); and ii) viability of cells determined by the MTT assay utilizing previously described techniques (Alley M C, Scudiero D A, Monks A, et al.: Feasibility of drug screening with panels of human tumor cell lines using a microculture tetrazolium assay, *Cancer Res* 40:589–601, 1988).

Clonogenic Potential of Treated Cells

Clonogenic potential of the treated human prostate cancer cells was determined on 24-hour-old cells seeded in 60 mm disposable dishes ($1-2\times10^2$ cells/dish). The cells were exposed to Rh-123 for 24,48, or 72 hours in triplicate sets at final concentrations of 1–50 µg/ml. They were then washed, and reincubated with Rh-123-free culture medium for 10–14 days before fixation, staining, and counting of colonies consisting of eight or more cells. Data are shown in FIGS. 2–7 relative to the number of colonies observed in control (untreated) cultures carried in parallel and represent results confirmed by repeat experiments.

Cytotoxicity of Human Prostate Cancer Cells Due to Rh-123

Cytotoxicity due to Rh-123 treatment was determined with the human prostate cancer cells grown in 96-well disposable microtiter plates. The cells were seeded at 2.5–4×1 cells per well and allowed to grow in normal culture medium for 2–3 days to obtain cells in exponential growth phase. The cells were then exposed to various Rh-123 concentrations (in sets of eight wells per concentration) spanning the range of 0–80 µg/ml by adding appropriate amounts of sterile Rh-123 stock solution (25 mg/ml Rh-123 in 95% by volume ethyl alcohol in sterile water) to an initial row, and serial dilutions in the subsequent rows of cells with an automatic dispensing device to obtain the desired range of concentrations for each experiment. Each plate had one row of cells not exposed to Rh-123 to serve as control cultures. Cytotoxicity determinations were done daily over a period of 1–8 days of Rh-123 exposure. Two microtiter plates were taken for each time point tested, with one used for immediate viability assessment and the other for testing the ability of Rh-123-treated cells to recover and grow following termination of exposure. For this, medium from wells of the treated plates was completely removed and the wells washed with serum-free medium before incubation with fresh 10% FBS (fetal bovine serum) containing DMEM/FI2 culture medium for a subsequent 2–5 days before subjecting to cell viability determinations.

Determination of Viability of Human Prostate Cancer Cells

Determination of viability of the human prostate cancer cells in the microtiter plates was done by incubation of the cells with 0.4 mg/ml MTT for 4 hours at 37° C., subsequent removal of the medium, and dissolving the cell bound dye in 150 µl DMSO. The plates were next read at $A_{540}$ µm with an Emax precision microplate reader (Molecular Devices Corporation, Menlo Park, Calif.). MTT is reduced to an insoluble formazan by mitochondria in living cells. The cell-bound dye is dissolved with DMSO and spectrophotometrically quantitated by absorbance at a wavelength of 540 nm. The $OD_{540}$ nm reading is a measure of the number of viable cells present in the test sample. Growth inhibition due to Rh-123 treatment was determined relative to readings obtained with control (untreated) culture wells on each microtiter plate. Results were confirmed by two to three repeat experiments with each cell line.

Retention of Rh-123 by Human Prostate Cancer Cells In Vitro

Rh-123 retention by the human prostate cancer cells was determined by flow cytometry utilizing an EPICS Profile II Flow Cytometer (Coulter Corp., Miami, Fla.). Subconfluent cell cultures were exposed to Rh-123 for 1 hour, washed, and incubated for 24 hours in Rh-123-free culture medium. Rh-123 uptake and retention was determined by comparing fluorescence intensities (at an excitation wavelength of 488 nm) of 10,000 cells collected immediately after 1-hour Rh-123 exposure and 24 hours after termination of Rh-123 exposure.

Rh-123 Cytotoxicity on Human Prostate Cancer Cells In Vitro

Figure 4:
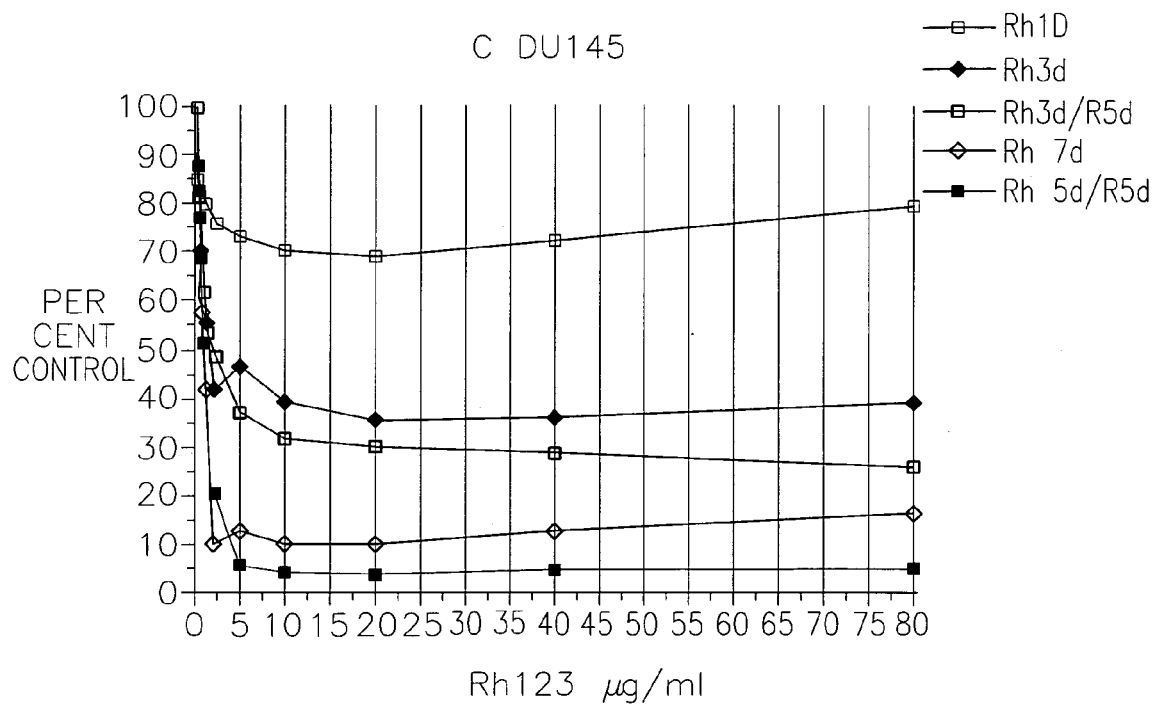
FIG. 4 shows the effect of Rh-123 exposure over a 0–80 µg/ml concentration range in DU-145 prostate cancer cells.
Figure 5:
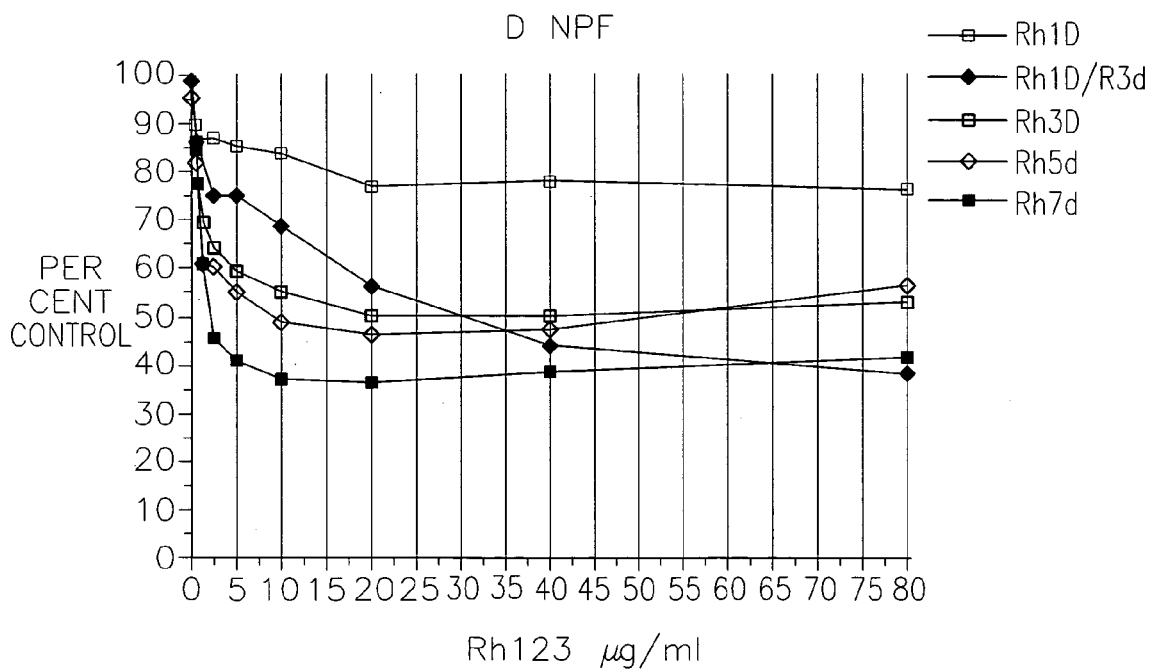
FIG. 5 shows the effect of Rh-123 exposure over a 0–80 µg/ml concentration range in NPF non-tumorigenic, diploid prostate cancer cells.
Figure 6:
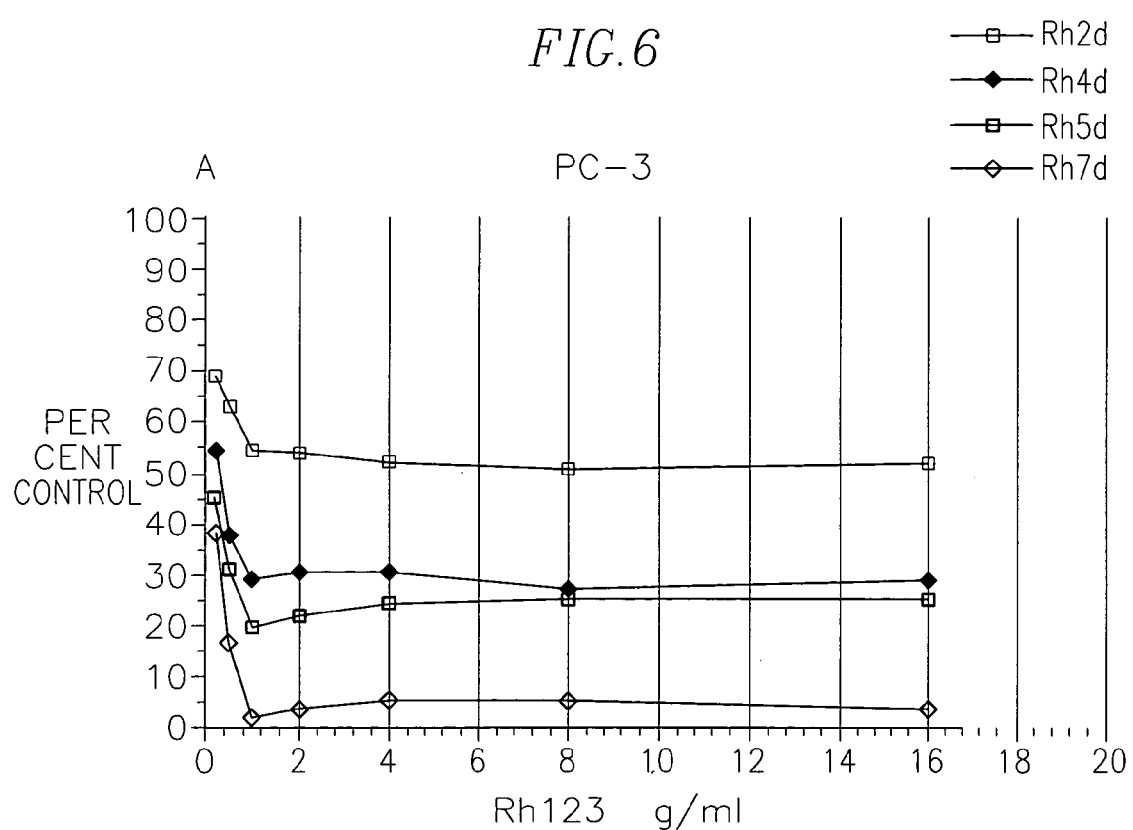
FIG. 6 is a graph showing growth inhibition in PC-3 prostate cancer cells due to Rh-123 exposure at concentrations of 0–16 µg/ml for 1–7 days.
Figure 7:
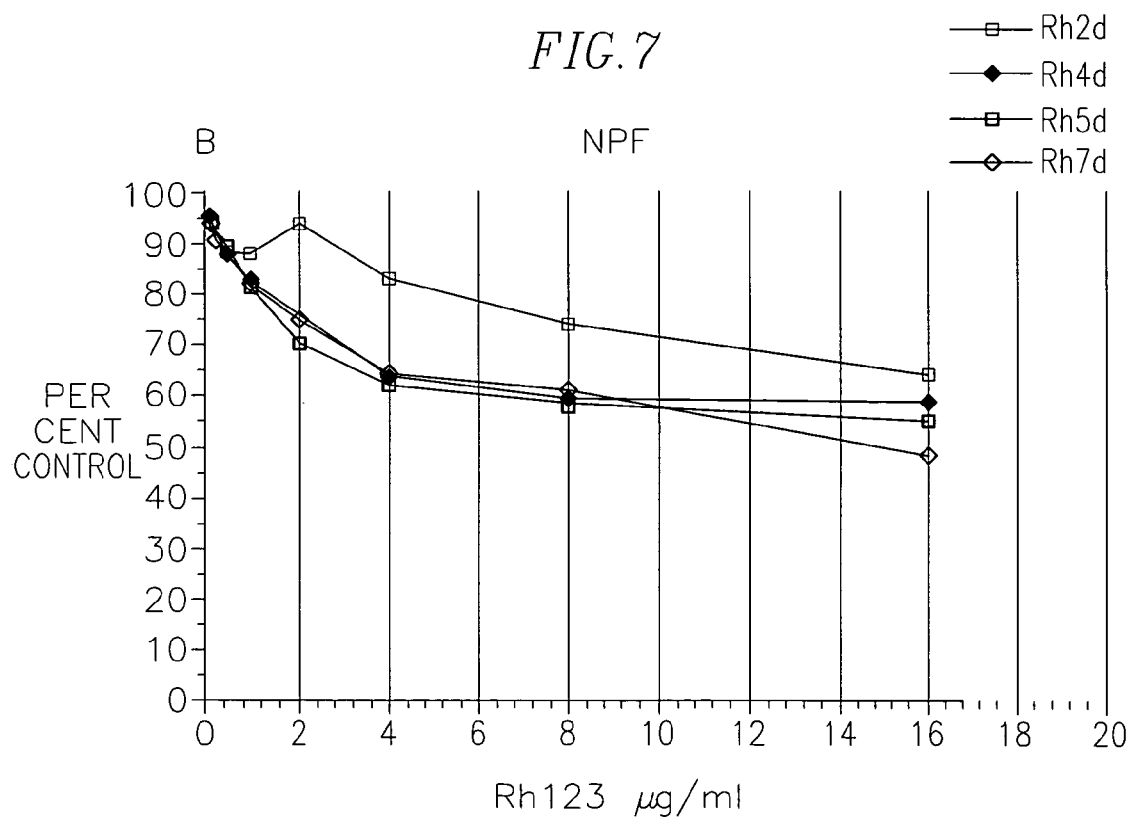
FIG. 7 shows growth inhibition in NPF non-tumorigenic prostate fibroblast due to Rh-123 exposure at concentrations of 0–16 µg/ml for 1–7 days.
Figure 8:
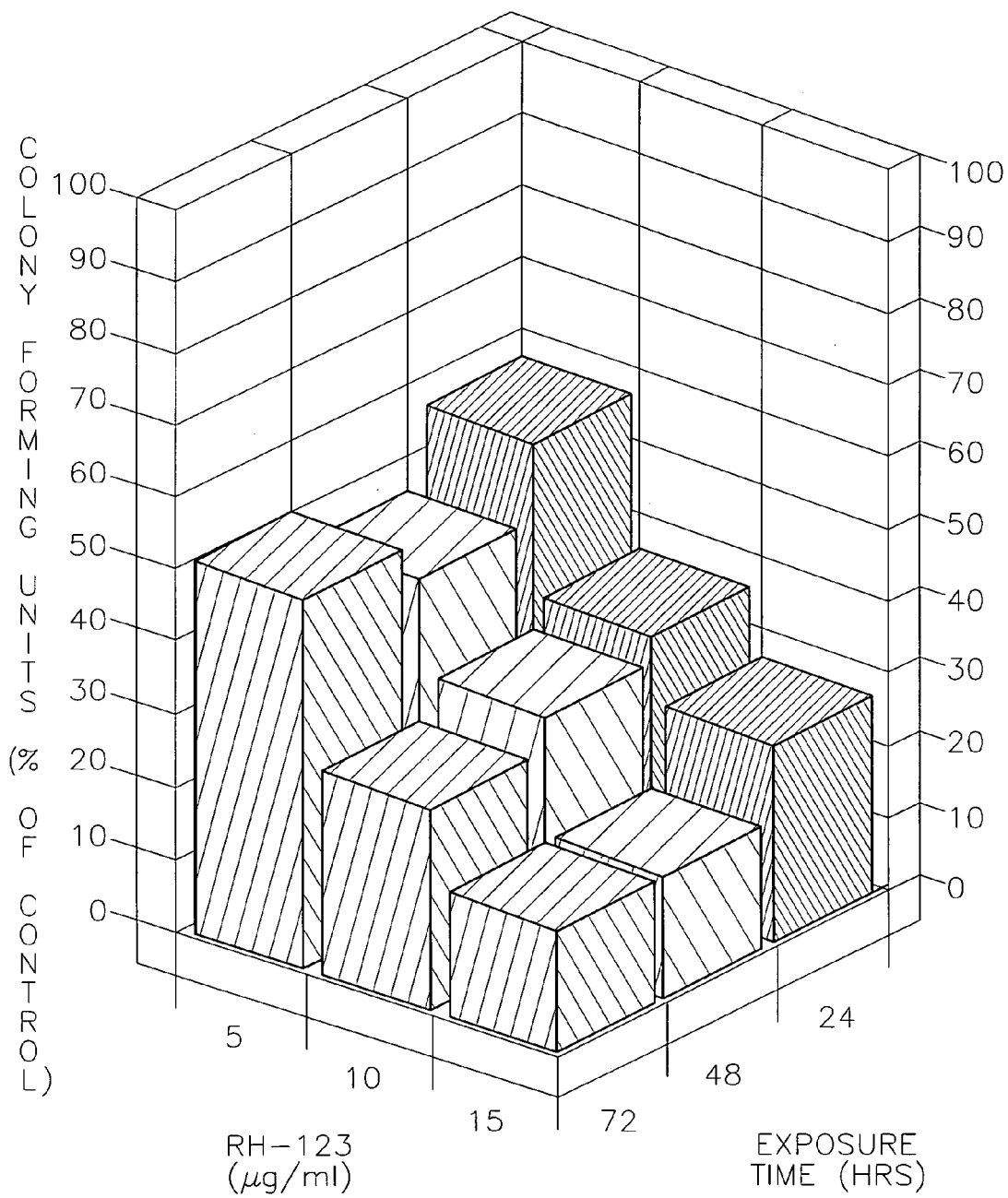
FIG. 8 is a three-dimensional bar graph showing the effect of Rh-123 on colony growth in NPF non-tumorigenic prostate cells.
Figure 9:
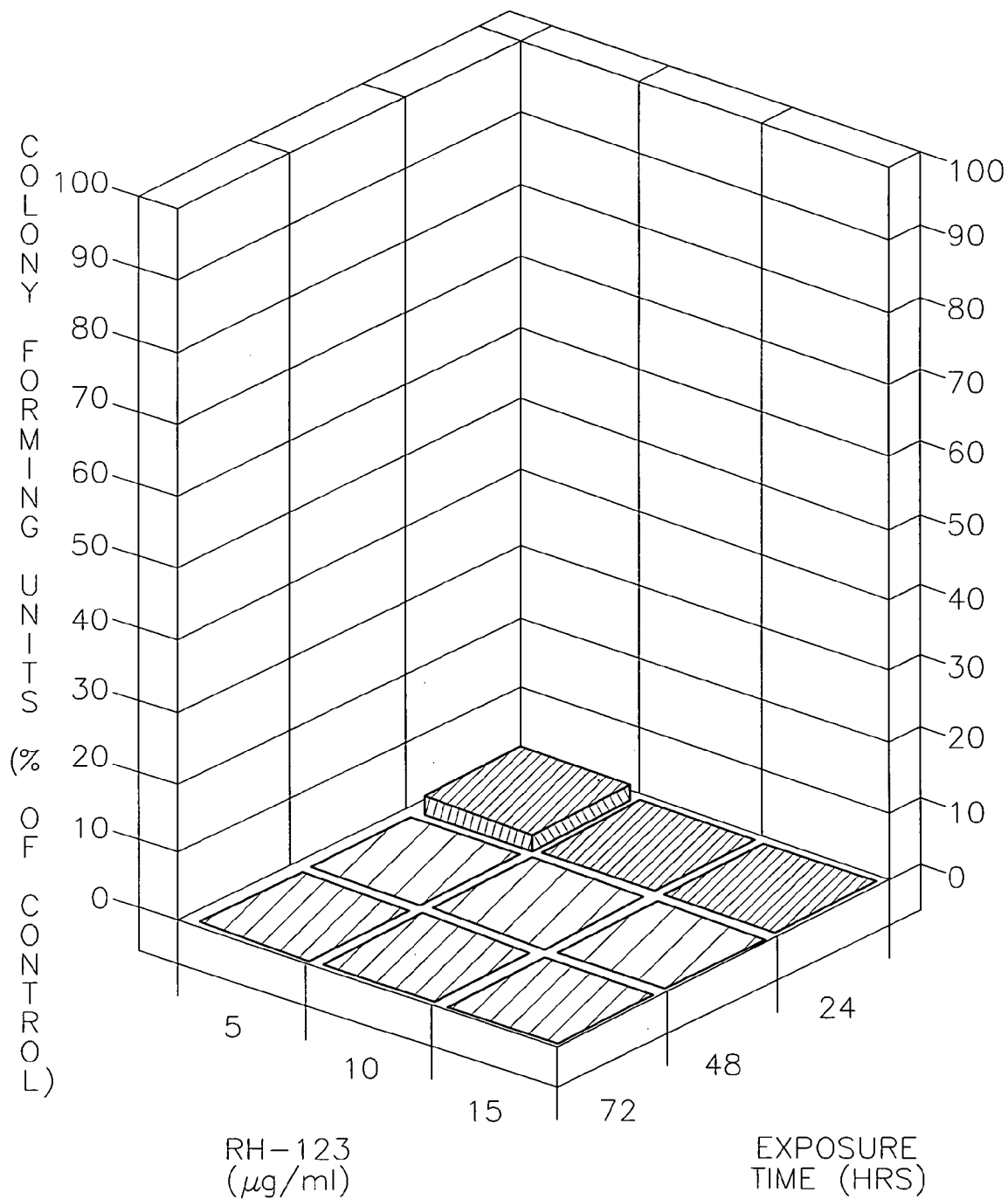
FIG. 9 is a bar graph similar to FIG. 8 showing the effect of Rh-123 on colony growth in PC-3 prostate cancer cells.
Figure 10:
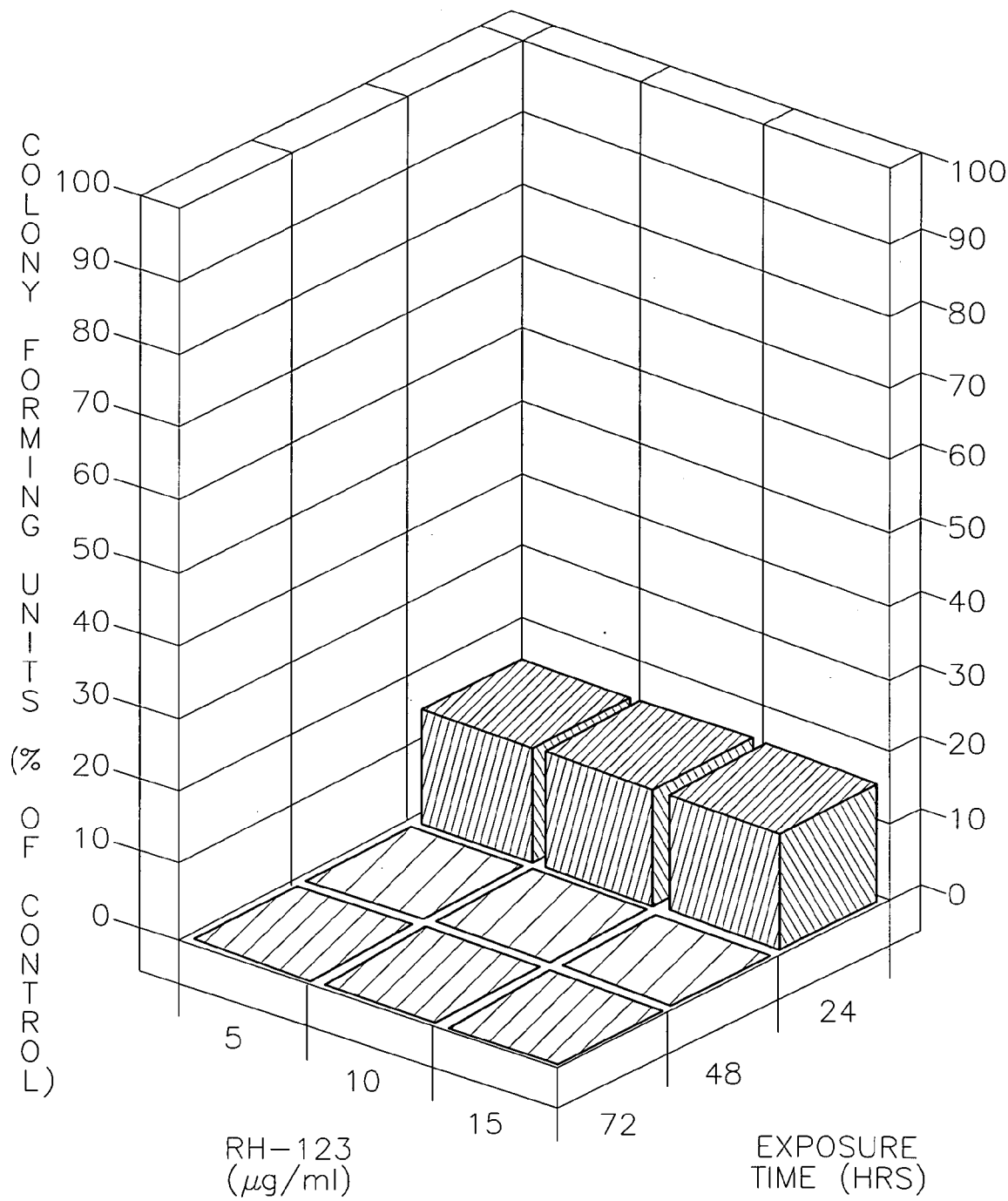
FIG. 10 is a bar graph similar to FIGS. 8 and 9 showing the effect of Rh-123 on colony growth in DU-145 prostate cancer cells.
Figure 11:
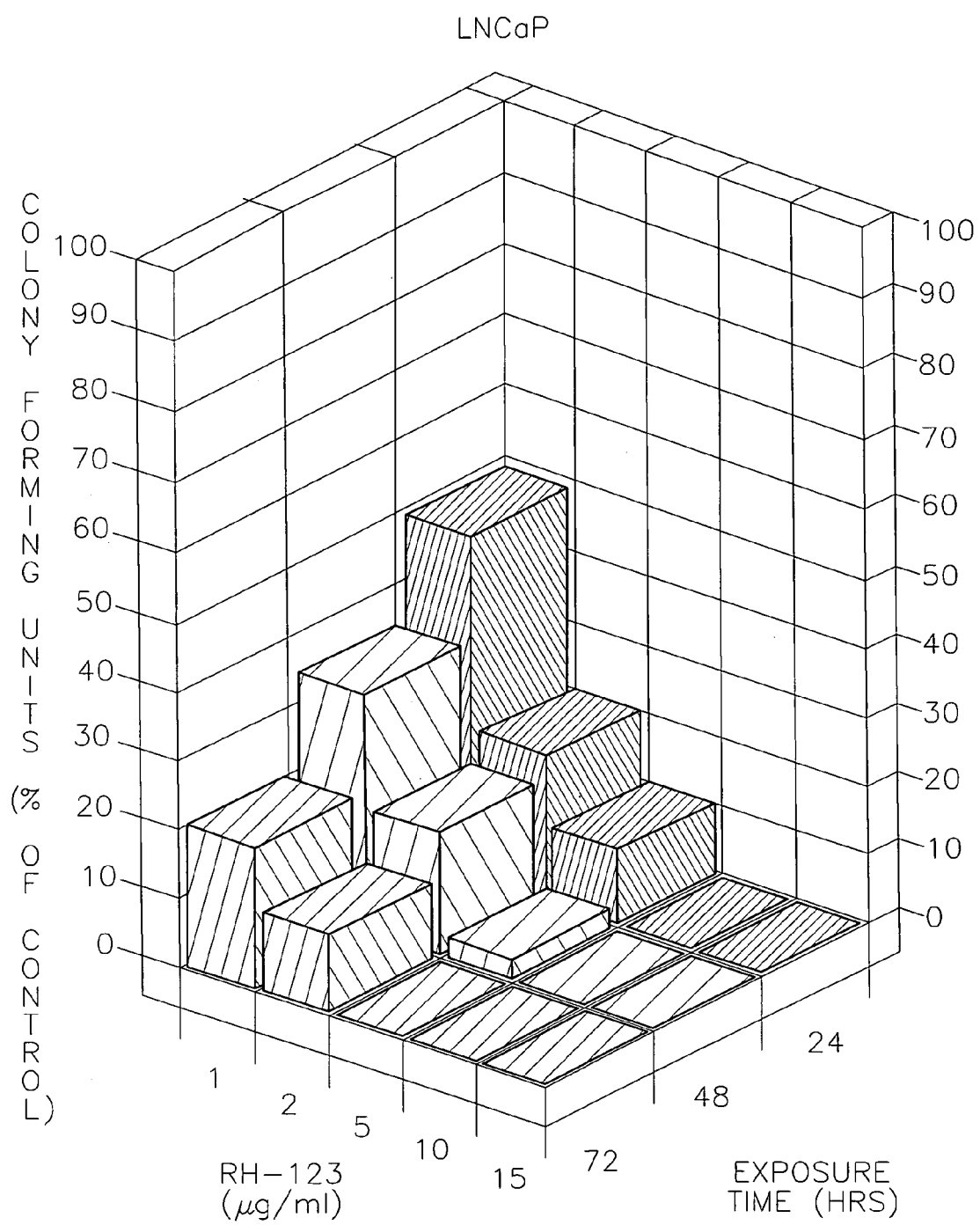
FIG. 11 is a bar graph similar to FIGS. 8–10 showing the effect of Rh-123 on colony growth in LNCaP prostate cancer cells.

FIGS. 2–7 represent data obtained in repeat experiments with the different human prostate cancer cells studied following exposure to 0–80 µg/ml of Rh-123 for a period of 1–7 days. FIGS. 2–5 compare the cytotoxic effects observed with the different cells over a broad (0–80 µg/ml) range of Rh-123 concentrations. FIGS. 6–7 show data from a different experiment covering a narrower range (0–16 µg/ml) of Rh-123 concentrations.

Figure 2:
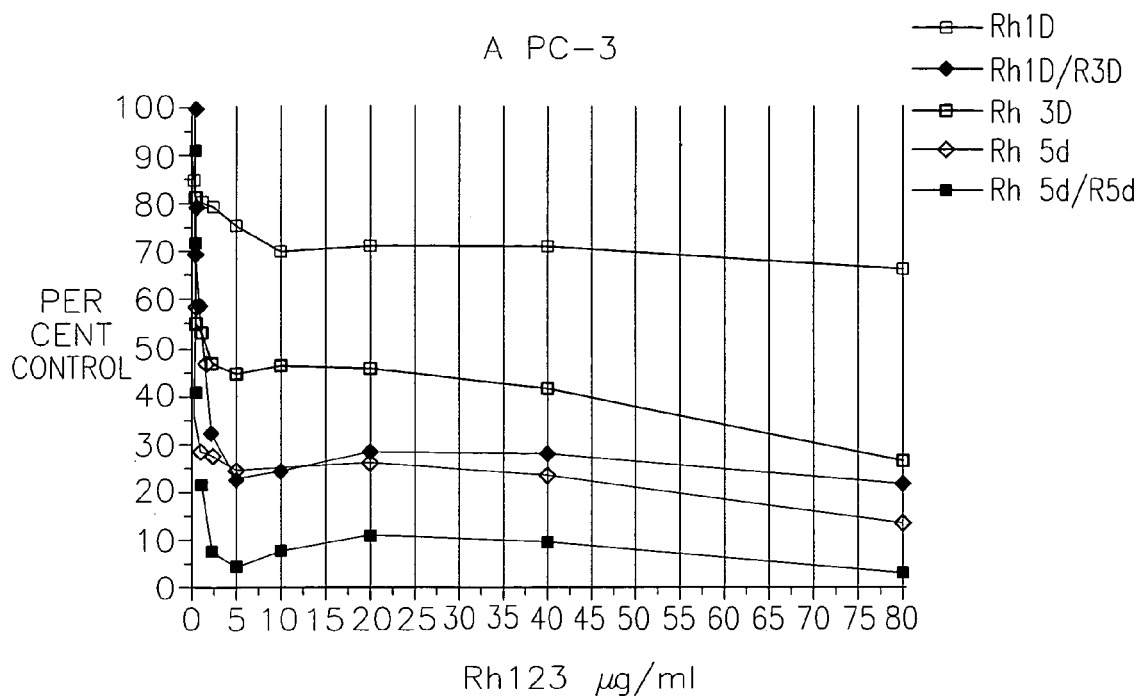
FIG. 2 is a graph showing the effect of Rh-123 exposure over a 0–80 µg/ml concentration range in PC-3 prostate cancer cells.

FIG. 2 shows the effect of Rh-123 exposure over a 0–80 µg/ml concentration range on PC-3 prostate cancer cells. The data are shown as percent viable cells (expressed relative to the viable cells in control (untreated)-sister wells) present following exposure to different Rh-123 concentrations for one, two, three, five, or seven days. Values shown for each Rh-123 concentration are averages of 8 or 16 duplicate wells. Viability of cells were determined as described above. The abbreviations, Rh1d, Rh2d, Rh3d, Rh5d, and Rh7d, stand for cells exposed to Rh-123 continuously for one, two, three, five, or seven days, respectively. Rh1d/R3d refers to cells exposed to Rh-123 for one day, plus recovery in normal growth medium for three days before cell viability assessment. Rh3d/R5 refers to Rh-123 exposure for three days, plus recovery for five days for cell viability assessment. Rh7d/R3 refers to Rh-123 exposure for seven days, plus three days recovery period in normal growth medium before cell viability assessment.

Figure 3:
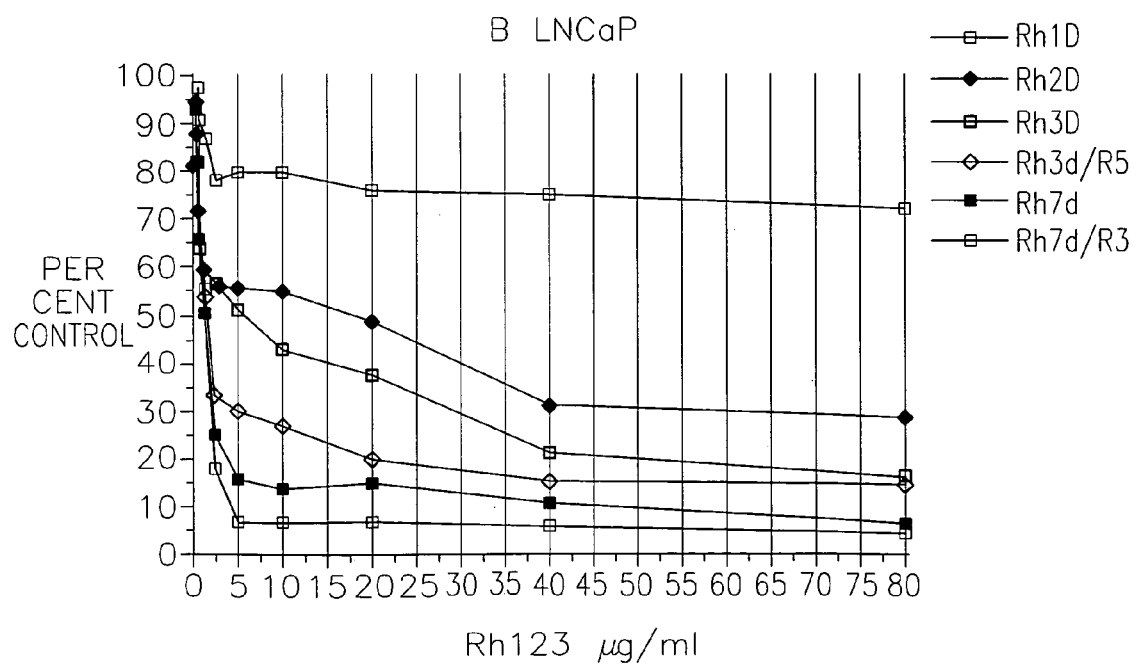
FIG. 3 shows the effect of Rh-123 exposure over a 0–80 µg/ml concentration range in LNCaP prostate cancer cells.

FIG. 3 shows the effect of Rh-123 exposure over a 0–80 µg/ml concentration range on LNCaP prostate cancer cells. The data were taken from the same experiment as described for FIG. 2, and the same abbreviations and other details apply.

FIG. 4 shows the effect of Rh-123 exposure over a 0–80 µg/ml concentration range on DU-145 prostate cancer cells. The data are from the same experiment as described for FIG. 2.

FIG. 5 shows the effect of Rh-123 exposure over a 0–80 µg/ml concentration range in NPF non-tumorigenic diploid prostate cells. Note that the growth inhibition due to Rh-123 treatment is much less than that observed with tumorigenic cells shown in FIGS. 2, 3, and 4. The data for FIG. 5 were taken from the same experiment as described for the data of FIG. 2.

The loss of viable cells was marked in all three types of human prostate cancer cells (PC-3, LNCaP, and DU-145) exposed for 2 days or longer to Rh-123 at concentrations as low as 1.25–2 μg/ml. In contrast, viability of NPF non-tumorigenic diploid cells remained relatively high even after prolonged Rh-123 exposures (FIGS. 2–7). The extent of cytotoxic effects was somewhat different in the three human prostate cancer cell lines. The PC-3 cells appeared to be the most sensitive to Rh-123 exposure. The DU-145 cells appeared to be more refractory than either the PC-3 or the LNCaP cells. There were no significant increases in cytotoxic effects on the cells at Rh-123 concentrations higher than 10 μg/ml (FIGS. 2–5). Recovery of Rh-123-treated prostate cancer cells incubated in Rh-123-free, normal growth medium was poor. The proportionate loss in viable cells remained the same or became more acute, suggesting continued loss of viable cells or inhibition of growth, despite restoration to normal growth media (see FIGS. 2–5).

Clonogenic assays (FIGS. 8–11) showed that colony growth of the PC-3 and LNCaP cells was greatly suppressed following exposure to 10 μg/ml of Rh-123. Growth suppression due to Rh-123 was less marked in the DU-145 cells. Complete suppression of colony growth in all three cancer cell lines was noted following Rh-123 10 μg/ml exposure for 72 hours. There was less dose-dependent suppression of normal human adult prostate fibroblasts with maximal suppression (28% of control) following a 72-hour exposure. Total suppression was not achieved even after a 72-hour exposure to 50 μg/ml (data not shown).

The above data correlated well with Rh-123 retention obtained by flow cytometry (see the TABLE below). Significant amounts of Rh-123 (73–64%) were retained by the three cancer cell lines, 24 hours after withdrawal of Rh-123. In contrast, over 90% of the Rh-123 taken up by NPF cells was lost within 24 hours following removal of the drug. Thus, these data suggest that the increased toxicity of Rh-123 for the treated prostate cancer cells was due to their selective retention of the drug.

The following table shows cell retention of Rh-123 after 24 hours in dye-free medium. Relative dye retention was estimated from the shift in mean fluorescence after Rh-123-labeled cells were allowed to recover in dye-free medium for 24 hours. Mean fluorescence values were normalized to 100% at 1 hour labeling with 10 μg/ml Rh-123.

TABLE (Retention of RH-123 After 24 Hours in Dye-Free Medium)

| Cell line | % Retention of Rh-123 |
| --- | --- |
| Human prostatic carcinoma | |
| DU-145 | 23 |
| LNCaP | |
| Population 1 | 24 |
| Population 2 | 64 |
| PC-3 | 40 |
| Normal prostate fibroblast | |
| NPF-209 | 9 |

Although the destructive effect of Rh-123 on cells in vitro has been reported by several authors (Lampidis, et al: Selective killing of carcinoma-cells in vitro by lipophilic-cationic compounds: A cellular basis, *Biomed Pharmacother* 39:220–226, 1985; Lampidis, et al: Selective toxicity of Rhodamine-123 in carcinoma cells in vitro, *Cancer Res* 43:716–720, 1983; Bernal, et al: Rhodamine-123 selectively reduces clonal growth of carcinoma cells in vitro, *Science* 218:1117–1118, 1982; Bernal, et al: Anticarcinoma activity in vivo of Rhodamine-123, a mitochondrial-specific dye, *Science* 222:169–172, 1983), there are few reports of its effect on in vivo solid tumors (Herr, et al: Anticarcinoma activity of Rhodamine-123 against a murine renal adenocarcinoma, *Cancer Res* 48:2061–2063, 1988). My previously reported studies (Arcadi J A: Rhodamine-123 as effective agent in rat prostate tumor R3327-H, *Urology* 28:501–503, 1986; Arcadi J A: Use of Rhodamine-123 in the treatment of the Pollard III rat prostate adenocarcinoma, *Surg Oncol* 44:103–108, 1990), as well as a large series of rats with transplantable tumors treated successfully with Rh-123 indicate that Rh-123 can destroy transplanted prostate tumors in rats.

My studies presented above, and also reported in my paper (Arcadi, et al: Studies of Rhodamine-123: Effect on Rat Prostate Cancer and Human Prostate Cancer Cells in Vitro, *Journal of Surgical Oncology*, 59:86–93 (1995)), demonstrated cell destruction by Rh-123 in an autochthonous rat prostate adenocarcinoma with a dose given for a short duration, and also, the preferential sensitivity of three different human prostate cancer cell lines.

The following protocol sets forth a procedure for using RH-123 to treat a patient with prostate cancer.

PROTOCOL

Criteria for admission:
  1) Metastatic hormone-resistant prostatic carcinoma
  2) Rising PSA Criteria for exclusion:
  1) Known cardiomyopathy
  2) Poor performance score
  3) Limited life expectancy (<90 days)

Study parameters:
  CPK, EKG, PSA, prostate specific acid phosphatase, and creatine 3 times during week of administration:
  Weekly: History, physical, performance score, CBC, biochemical profile, PSA, prostate specific acid phosphatase, and EKG Stock solution:
  25 mg/ml in 95% (by volume) ethanol in water Final Preparation:
  Indicated dose (see below) added 5DW (5% by weight dextrose in sterile water) to a final concentration of 5% ethanol Mode of Administration:
  4 hour i.v. infusion or about 100 ml/hr., whichever is slower Cycle:
  Monthly

| | Part A | | | | | | |
| --- | --- | --- | --- | --- | --- | --- | --- |
| Part/Week | A/0 | A/1 | A/5 | A/9 | A/13 | A/17 | A/21 |
| Dose mg/kg | 0 | 1 | 2 | 5 | 10 | 20 | 30 |
| Frequency/cycle | — | 1 | 1 | 1 | 1 | 1 | 1 |

Criteria for progression to Part B: Any signs of toxicity

| Part B | | | | | | | |
|---|---|---|---|---|---|---|---|
| Part/Week | B/O | B/1 | B/5 | B/9 | B/13 | B/17 | B/21 |
| *Dose mg/kg | 0 | X | X | X | X | X | X |
| Frequency/cycle (every other day) | — | 1 | 2 | 3 | 4 | 5 | 6 |

*X = greatest non-toxic dose patient received under Part A
Criteria for termination: Signs of severe toxicity After being subjected to the indicated criteria for admission and exclusion, a patient is treated in 4-week cycles in accordance with Part A and then Part B of the above protocol. During the first week of administration of the treatment, conventional CPK, EKG, and creatine measurements are made on the patient three times to check for signs of toxicity. On a weekly basis, the patient is subjected to conventional physical tests, as well as complete blood count, biochemical profile, EKG, prostate specific acid phosphatase, and PSA measurements. For example, a patient with metastatic hormone-resistant prostate carcinoma may have a PSA level of about 100 nanogram/ml. A normal PSA reading is usually considered to be below about 4 nanogram/ml.

During the first week of Part A of the protocol, while the patient is observed and subjected to the various tests referred to above, no Rh-123 is administered. At the end of the first week, which is the beginning of the first 4-week cycle (A/1), the patient is given a 4-hour i.v. infusion of 250 ml of 5DW (5% dextrose by weight in sterile water) to which has been added an appropriate amount of stock solution to give the patient a dose equal to 1 mg of Rh-123 for each kg of body weight. For example, if the patient weighs 70 kg, 2.8 ml of stock solution (25 mg/ml Rh-123 in 95% ethyl alcohol and 5 water) are added to 250 ml 5 DW to make 252.8 ml of treatment solution which contains 70 mg Rh-123 and about 1% ethyl alcohol by volume. Additional ethyl alcohol can be added up to a total of about 5% by volume to ensure that the Rh-123 stays in solution.

At the beginning of the fifth week, i.e., the beginning of the second 4-week cycle (B/5), the same procedure is followed to give the patient a dose of 2 mg of Rh-123 per kg of body weight. The dose is increased to 5 mg/kg at the beginning of the ninth week by adding 14 ml of stock solution to 250 ml 5 DW to make 265 ml of treatment solution containing 35 mg of Rh-123 and about 5% ethyl alcohol by volume. For the 10 mg/kg dose at the beginning of the thirteenth week, and for each dose thereafter, the treatment solution is diluted with sufficient 5 DW to bring the concentration of the ethyl alcohol down to about 5% by volume, although the solution could be used with the alcohol content at a maximum of 10% by volume, depending on the patient. The procedure is continued as indicated by Part A of the above protocol until the patient shows signs of toxicity, or reaches a dose at a level of 30 mg/kg (84 ml of stock solution in 1591.8 ml of 5DW, for a total of 1675.8 ml of treatment solution containing about 5% ethyl alcohol by volume).

Of course, Part A of the treatment can start at a lower level of Rh-123, say, 0.2 to 0.5 mg/kg of body weight, if desired. Accordingly, the treatment solution will include between about 0.2% and about 5% ethyl alcohol by volume. If the concentration of alcohol in the treatment solution exceeds the comfort or tolerance level of the patient, the solution can be diluted, say, with 5DW, to an acceptable level, and be administered over a greater time period than 4 hours. In any event, for administering a treatment with a solution which exceeds about 400 ml, the infusion is normally done at a rate of no more than about 100 ml/hr.

By way of example, if the patient shows signs of toxicity between the ninth and twelfth weeks (i.e., during the third 4-week cycle (A/9)) when the dose under Part A was 5 mg/kg and caused toxicity), treatment is terminated until signs of toxicity disappear. The patient is then treated in accordance with Part B of the protocol, i.e., with a single dose of 2 mg Rh-123 per kg of body weight (i.e., the greatest non-toxic dose given to the patient under Part A of the protocol) every other day for the indicated frequency for each cycle to the end of treatment which begins with the 21st week, unless the patient previously shows signs of severe toxicity, or the patient's PSA level drops below about 4. For example, at the beginning of the first week of the first cycle (B/1), the patient is given the indicated dose on the first day for a total of one dose for the first four-week cycle. Then, at the beginning of the 5th week (second four-week cycle, B/5), the patient is given the dose on the first and third days for a total of two doses for the second four-week cycle. The procedure is continued, as needed, until the beginning of the 21st week (sixth cycle, B/21), when the patient is given the dose on the 1st, 3rd, 5th, 7th, 9th, and 11th days, for a total of six doses for the sixth four-week cycle. Thereafter, the patient is monitored with tests as described above, and the treatment is repeated, as necessary, to keep his PSA level below about 4, or to the point of toxicity, whichever occurs first.

The FDA has approved human clinical Phase I study of Rh-123. This phase evaluates the toxicity of Rh-123. The objective of the study is to determine safe dosing levels for Rh-123 starting at a level known to be safe for animals (about 0.3 mg/kg, which is equivalent to about 12 mg/m$^2$ for the typical prostate cancer patent), and proceeding upward in dosage until signs of moderate toxicity are observed. The Phase I study includes 21 volunteer patients with metastatic hormone-refractory prostate cancer to establish toxicity in a single dose escalation schedule. Only one dose per volunteer participant has been approved to date by the FDA, starting at 12 mg/m$^2$ at level I (three participants per level), and increasing in subsequent levels until dose-limiting toxicity is observed.

Using a solution of four milligrams of Rh-123 per milliliter of a solution which includes 5% alcohol and 5% glucose in distilled water, the FDA has approved the dose escalation schedule shown in Table I:

TABLE I

| Level | No. of Patients per Level | Rh-123 per Body Surface Area (BSA) (mg/m$^2$) |
|---|---|---|
| I | 3 | 12 |
| II | 3 | 24 |
| III | 3 | 48 |
| IV | 3 | 96 |
| V | 3 | 135 |
| VI | 3 | 189 |
| VII | 3 | 265 |

By way of example, a patent with a body surface area of 1.73 m$^2$ treated at Level VII would receive a total infusate volume of 115 milliliters.

As of the date of this application for patent, seven patients have been treated in accordance with the protocol described above. Table II shows how the amount of prostate specific acid phosphatase in blood samples varied over time for some of the patients treated with a single does of Rhodamine-123 as described above.

TABLE II

| Patient No. (Level of dose) | Entry | 24 hrs | 48 hrs | 96 hrs | 2 weeks | 1 month | 2 months | 3 months | 4 months | 5 months | 6 months |
|---|---|---|---|---|---|---|---|---|---|---|---|
| 1 (I)   | —    | — | —      | —      | —     | —     | 1.23  | 1.40   | —     | —     |   |
| 2 (I)   | —    | — | —      | —      | —     | —     |       | 8.9    |       | 35.1  |   |
| 3 (I)   | —    | — | 32.3   | 26     | 62.3  | 1.90  | 45.8  | —      | 79.5  | —     |   |
| 4 (II)  | —    | — | 1079.0 | 1076.0 | 724.0 | 402.0 | 253.0 | 1020.0 | 438.0 | 722.0 |   |
| 5 (II)  | —    | — | 31.9   | —      | 41.7  | 25.1  | 11.1  | —      | 63.0  |       |   |
| 6 (II)  | 24.4 | — | 25.6   | 27.7   | 23.9  | 26.7  | 23.0  | 58.5   |       |       |   |
| 7 (III) | 8.1  | — | 5.6    | 7.2    | 8.0   | 6.8   | 8.2   | 9.1    |       |       |   |

Table II shows that patient No. 4 (treated at Level II, i.e., 24 mg Rh-123/per m$^2$) had a prostate specific acid phosphatase reading of 1079.0 mg/ml 48 hours after initial infusion. Thereafter, the amount of prostate specific acid phosphatase in that patient's blood steadily decreased until two months after the infusion, and then began to increase again. Thus, even this limited treatment indicates encouraging effect on prostate cancer for patient No. 4. It should be kept in mind that the Phase I study is intended to set toxicity limits. Criteria for satisfactory response and progression for treatment of hormone-refractory prostate cancer are raw survival, changes in hemoglobin, PSA level, and level of acid phosphatase. These parameters will be noted and incorporated into the Phase II study planned for Rhodamine-123.

The Rh-123 can be administered to the patient by procedures other than i.v. administration. For example, a convenient method of administering Rh-123 to a patient with prostate cancer is by oral administration, either in the form of a liquid solution, or as a pill, such as a tablet or capsule, at appropriate intervals to effect in vivo destruction of prostate cancer cells to an extent which lowers the PSA count in the patient's blood to a level substantially below that which prevailed before treatment began. If the patient is susceptible to toxic effects from oral administration of Rh-123, the medication is incorporated in an enteric tablet or capsule in which particles of Rh-123 are coated to be released in the intestines over a relatively long period of time, say, 2–15 mg of Rh-123 per kilogram of body weight over an interval of about 2 to about 24 hours. Formulation of the medication into capsules or tablets to provide the required time release is done by routine procedures well known to those skilled in the art.

Ideally, after a patient's tolerance to Rh-123 is established, that patient can take a prophylactic dose of Rh-123 at appropriate levels and intervals to inhibit the proliferation of prostate cancer cells, and keep the patient's PSA level at a safe value, say, less than 4 or 5 nanograms per ml.

What is claimed is:

1. A method for treating prostate carcinoma in a patient comprising intravenous administration of a solution of Rhodamine-123 in ethyl alcohol and water in an amount sufficient to effect in vivo destruction of prostate carcinoma cells.

2. A method for treating prostate cancer in a patient who has a PSA level above about 5, the method comprising measuring the PSA level in the blood of the patient, administering Rhodamine-123 to the patient in an amount sufficient to effect in vivo destruction of prostate cancer cells, and thereafter measuring the patient's PSA level to confirm the destruction of prostate cancer cells in the patient.

3. The method according to claim 2 wherein said step of measuring the patient's PSA level is done before and after treatment, and administering sufficient Rhodamine-123 to substantially decrease the level of PSA in the blood of the patient.

4. The method according to claim 1, 2 or 3 which includes injecting the patient with about 250 ml of a solution containing Rhodamine-123.

5. The method according to claim 1, 2, or 3 in which the administration of Rhodamine-123 is completed within about four hours.

6. The method according to claim 1, 2, or 3 in which the patient is treated with up to about 30 mg Rhodamine-123 per kg of body weight every other day.

7. The method according to claim 1, 2, or 3 in which the patient is treated with between about 0.2 and about 15 mg of Rhodamine-123 per kg of patient body weight.

8. The method according to claim 1, 2, or 3 in which the patient is administered the solution of Rhodamine-123 at intervals of at least 24 hours, and in increasing amounts until the patient exhibits evidence of toxicity due to the Rhodamine-123, and thereafter administering Rhodamine-123 to the patient in an amount and at a rate less than that which causes toxicity.

9. A solution which treats carcinoma in a patient comprising ethyl alcohol and an effective amount of Rhodamine-123 dissolved in water.

10. The solution according to claim 9 which includes dissolved sugar susceptible to metabolic assimilation.

11. The solution according to claim 10 in which the sugar is selected from the group consisting of dextrose, glucose, and fructose.

12. The solution according to claim 10 or 11 in which the sugar is present by an amount equal to about 5% by weight.

13. The solution according to claim 9, 10, or 11 in which the ethyl alcohol is present in an amount between about 0.2% and about 5% by volume.

14. A stock solution for preparing an administration solution which treats carcinoma in a patient, the stock solution comprising Rhodamine-123 dissolved in ethyl alcohol.

15. The stock solution according to claim 14 in which the solution contains about 95% ethyl alcohol by volume and about 5% sterile water by volume.

16. The solution according to claim 14 or 15 in which the Rhodamine-123 is present in an amount between about 4 and about 25 mg/ml of solution.

17. A method for treating prostate cancer in a patient who has a PSA level above about 5, the method comprising oral administration of Rhodamine-123 in a pill which releases the Rhodamine-123 for absorption by the patient, and in an amount sufficient to effect in vivo destruction of prostate cancer cells in the patient, measuring the patient's PSA level after treatment, and thereafter administering Rhodamine-123 to the patient at a rate sufficient to substantially decrease the patient's PSA level.

18. The method according to claim 17 in which the pill releases between about 0.2 and about 30 mg of Rhodamine-123 per kg of patient body weight.

19. The method according to claim 17 or 18 in which the Rhodamine-123 is released within between about 2 and about 24 hours.

20. A method for treating prostate carcinoma in a patient with prostate carcinoma, the method comprising treating the patient by dissolving Rhodamine-123 in a solvent which includes ethyl alcohol to form a stock solution, diluting the stock solution with water to form a treatment solution which includes Rhodamine-123, water and ethyl alcohol, and administering the treatment solution to the patient in an amount sufficient to effect in vivo destruction of prostate carcinoma cells.

21. The method according to claim 20 which includes the step of measuring the patient's PSA level before and after treatment, and administering sufficient Rhodamine-123 to substantially decrease the level of PSA in the blood of the patient.

22. The method according to claim 20 or 21 which includes injecting the treatment solution intravenously.

23. The method according to claim 20 or 21 in which the stock solution contains between about 4 and about 25 mg of Rhodamine-123 per liter.

24. The method according to claim 20 or 21 in which the treatment solution contains between about 0.2% and about 5% ethyl alcohol by volume.

25. A method for treating prostate cancer in a patient who has a PSA level above about 5, the method comprising measuring the prostate specific acid phosphatase level in the blood of the patient, administering Rhodamine-123 to the patient in an amount sufficient to effect in vivo destruction of prostate cancer cells, and thereafter measuring the patient's prostate specific acid phosphatase level to confirm the destruction of prostate cancer cells in the patient.

26. The method according to claim 25 which includes the step of measuring the patient's prostate specific acid phosphatase level before and after treatment, and administering sufficient Rhodamine-123 to substantially decrease the level of prostate specific acid phosphatase in the blood of the patient.

27. A method for treating prostate cancer in a patient comprising dissolving Rhodamine-123 in a solvent which includes ethyl alcohol to form a stock solution, diluting the stock with water to form a treatment solution which includes Rhodamine-123, water and ethyl alcohol, administering the treatment solution to the patient in an amount sufficient to effect in vivo destruction of prostate cancer cells, measuring the patient's prostate specific acid phosphatase level before and after treatment, and administering sufficient Rhodamine-123 to substantially decrease the level of prostate specific acid phosphatase in the blood of the patient.

28. A method for treating carcinoma in a patient comprising intravenous administration of a solution of Rhodamine-123 in ethyl alcohol and water in an amount sufficient to effect in vivo destruction of carcinoma cells.

29. A method for treating carcinoma in a patient comprising administering Rhodamine-123 to the patient in an amount sufficient to effect in vivo destruction of carcinoma cells.

30. A method for treating prostate cancer in a patient comprising administering Rhodamine-123 to the patient in an amount sufficient to effect in vivo destruction of prostate cancer cells.

* * * * *